(12) United States Patent
Yamada

(10) Patent No.: US 11,096,609 B2
(45) Date of Patent: Aug. 24, 2021

(54) BRAIN FUNCTION MEASUREMENT DEVICE AND BRAIN FUNCTION MEASUREMENT METHOD

(71) Applicant: National Institute of Advanced industrial Science and Technology, Tokyo (JP)

(72) Inventor: Toru Yamada, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 682 days.

(21) Appl. No.: 15/542,193

(22) PCT Filed: Sep. 17, 2015

(86) PCT No.: PCT/JP2015/076465
§ 371 (c)(1),
(2) Date: Sep. 7, 2017

(87) PCT Pub. No.: WO2016/111056
PCT Pub. Date: Jul. 14, 2016

(65) Prior Publication Data
US 2019/0380634 A1 Dec. 19, 2019

(30) Foreign Application Priority Data
Jan. 7, 2015 (JP) .............................. JP2015-001795

(51) Int. Cl.
*A61B 5/1455* (2006.01)
*A61B 5/00* (2006.01)
(Continued)

(52) U.S. Cl.
CPC ...... *A61B 5/14553* (2013.01); *A61B 5/14552* (2013.01); *A61B 5/6814* (2013.01);
(Continued)

(58) Field of Classification Search
CPC ....................... G01B 2290/70; A61B 5/14552
See application file for complete search history.

(56) References Cited

U.S. PATENT DOCUMENTS

| 2004/0109164 A1* | 6/2004 | Horii | G01B 9/0201 356/479 |
| 2009/0290149 A1* | 11/2009 | Roth | G01N 21/3581 356/300 |

(Continued)

FOREIGN PATENT DOCUMENTS

| JP | 2001264246 A | 9/2001 |
| JP | 2003207443 A | 7/2003 |

(Continued)

OTHER PUBLICATIONS

Cui, X., et al.; "Functional near infrared spectroscopy (NIRS) signal improvement based on negative correlation between oxygenated and deoxygenated hemoglobin dynamics", NeuroImage 49 (2010); pp. 3039-3046; 2009 Elsevier Inc. DOI:10.1016/j.neuroimage.2009.11.050.

(Continued)

*Primary Examiner* — Yi-Shan Yang
(74) *Attorney, Agent, or Firm* — Cantor Colburn LLP

(57) ABSTRACT

Provided is a brain function measurement device capable of improving the reliability of brain function measurement using a simple configuration. The brain function measurement device includes light source probes LD2 and LD12 for irradiating the scalp of a test subject with light beams; linearly polarizing films P2 and P3 for polarizing the light beams emitted from the light source probes LD2 and LD12 in a first direction; a linearly polarizing film P1 for blocking components in the first direction of reflected light beams that are generated as the light beams emitted from the linearly polarizing film P2 and P3 are reflected by the hairs of the test (Continued)

subject; and a detection probe PD1 for detecting the intensity of a light beam that has passed through the linearly polarizing film P1.

4 Claims, 3 Drawing Sheets

(51) Int. Cl.
  *G01B 9/02* (2006.01)
  *G01N 21/359* (2014.01)

(52) U.S. Cl.
  CPC .......... *A61B 5/7207* (2013.01); *A61B 5/0064* (2013.01); *A61B 5/0075* (2013.01); *G01B 9/0205* (2013.01); *G01B 2290/70* (2013.01); *G01N 21/359* (2013.01)

(56) References Cited

U.S. PATENT DOCUMENTS

| | | | |
|---|---|---|---|
| 2011/0205535 A1* | 8/2011 | Soller | A61B 5/145 356/300 |
| 2012/0140231 A1* | 6/2012 | Knox | H01L 29/7786 356/442 |
| 2015/0223694 A1 | 8/2015 | Funane et al. | |

FOREIGN PATENT DOCUMENTS

| | | |
|---|---|---|
| JP | 2009136434 A | 6/2009 |
| JP | 2009240414 A * | 10/2009 |
| JP | 2009240414 A | 10/2009 |
| WO | 2014034285 A1 | 3/2014 |

OTHER PUBLICATIONS

Orihuela-Espina, F., et al.; "Quality control and assurance in functional near infrared spectroscopy (fNIRS) experimentation", Physics in Medicine and Biology, Phys. Med. Biol. 55 (2010); Published Jun. 9, 2010; pp. 3701-3724; IOP Publishing. DOI:10.1088/0031-9155/55/13/009.

Written Opinion for International Appliation No. PCT/JP2015/076465, International Filing Date Sep. 17, 2017, dated Dec. 12, 2015, 3 Pages.

International Search Report for International Application No. PCT/JP2015/076465, International Filing Date Sep. 17, 2015, dated Dec. 15, 2015, 1 Page.

Partial Translation of JP 2009-240414.

* cited by examiner

BRAIN FUNCTION MEASUREMENT DEVICE AND BRAIN FUNCTION MEASUREMENT METHOD

TECHNICAL FIELD

The present invention relates to a device and method for measuring the functions of brains.

BACKGROUND ART

In recent years, local changes in the cerebral blood flow that are associated with activities of cranial nerves have been observed non-invasively, using a near-infrared brain function measurement method (i.e., functional near-infrared spectroscopy: fNIRS) with probes placed on the head.

Herein, when the probes are placed from above hairs of the head, the positions of the probes are unstable because the gaps between the hairs are about 1 millimeter while the diameter of the tip end of each probe is usually several millimeters, which means that there is a layer of hairs between each probe and the scalp and such a layer functions as a type of cushion.

If measurement is conducted under such unstable position conditions of the probes and without the head of a test subject fixed, data containing motion artifacts that are a type of noise resulting from fluctuations of the probes due to motions of the test subject is observed. Therefore, as described in Non Patent Literature 1 and 2, techniques for removing such type of motion artifacts have been proposed.

CITATION LIST

Patent Literature

Patent Literature 1: 2009-136434 A

Non Patent Literature

Non Patent Literature 1: F. Orihuela-Espina, D. R. Leff, D. R. C. James, A. W. Darzi and G. Z. Yang, "Quality control and assurance in functional near infrared spectroscopy (fNIRS) experimentation", Phys. Med. Biol. 55 (2010), pp. 3710-3724

Non Patent Literature 2: Xu. Cui, Signe. Bray, Allan. L. Reiss, "Functional near infrared spectroscopy (NIRS) signal improvement based on negative correlation between oxygenated and deoxygenated hemoglobin dynamics", Neuro-Image. 49 (2010), pp. 3039-3046

SUMMARY OF INVENTION

Technical Problem

However, in the techniques described in Non Patent Literature 1 and 2, since the criterion for determining a fluctuation of a given signal to be a motion artifact is not necessarily said to be clearly defined from the perspective of the measurement theory, there are problems in that the resulting effect of removing motion artifacts differs from method to method or from model to model or depending on how the probes fluctuate.

The present invention has been made in order to solve the aforementioned problems, and it is an object of the present invention to improve the reliability of brain function measurement using a simple configuration or method.

Solution to Problem

In order to solve the aforementioned problems, the present invention provides a brain function measurement device, including light irradiation means for irradiating a scalp of a test subject with a light beam; first polarizing means for linearly polarizing the light beam emitted from the light irradiation means in a first direction; blocking means for blocking a component in the first direction of a reflected light beam that is generated as the light beam emitted from the first polarizing means is reflected by a hair of the test subject; and detection means for detecting an intensity of a light beam that has passed through the blocking means.

In addition, in order to solve the aforementioned problems, the present invention provides a brain function measurement method, including a first step of irradiating a scalp of a test subject with a light beam; a second step of linearly polarizing the light beam emitted in the first step in a first direction; a third step of blocking a component in the first direction of a reflected light beam that is generated as the light beam emitted in the second step is reflected by a hair of the test subject; and a fourth step of detecting an intensity of a light beam generated by the blocking in the third step.

Advantageous Effects of Invention

According to the present invention, the reliability of brain function measurement can be improved using a simple configuration or method.

DESCRIPTION OF EMBODIMENTS

Figure 1:
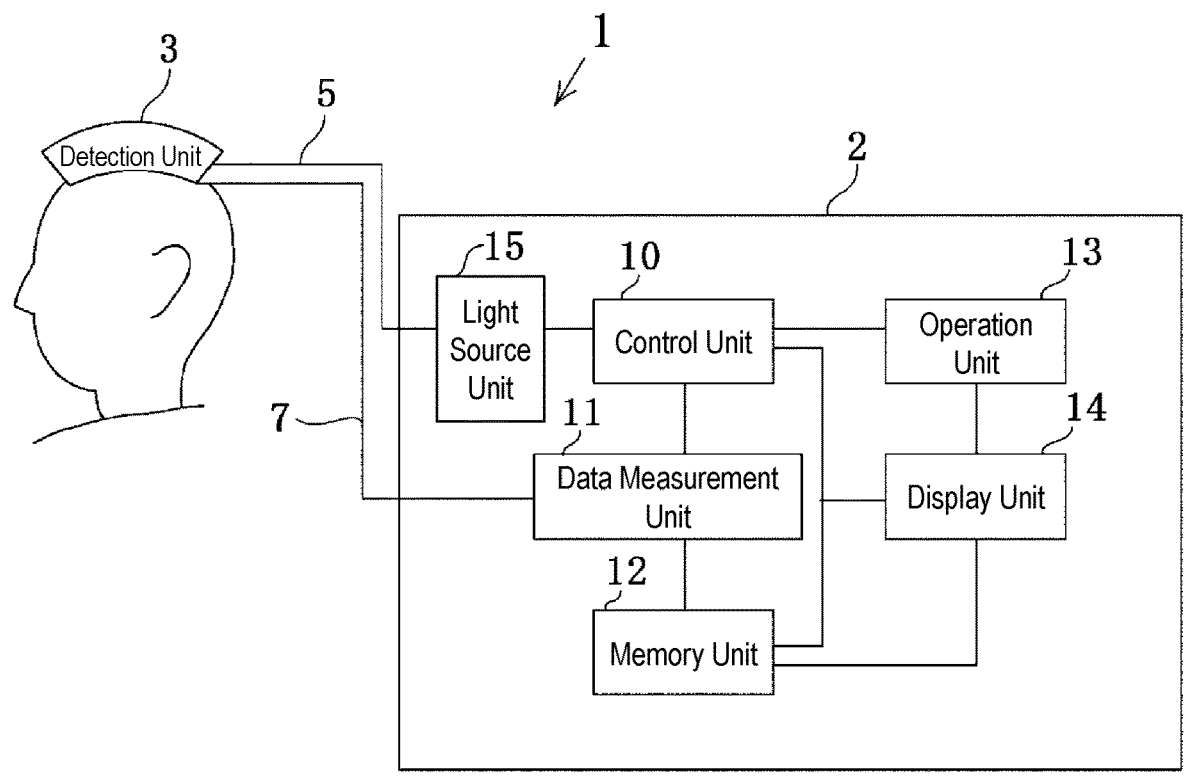
FIG. 1 is a block diagram illustrating the entire configuration of a brain function measurement device 1 in accordance with an embodiment of the present invention.

Hereinafter, embodiments of the present invention will be described in detail with reference to the drawings. In the drawings, identical reference numerals denote identical or corresponding portions.

FIG. 1 is a diagram illustrating the configuration of a brain function measurement device 1 in accordance with an embodiment of the present invention. As illustrated in FIG. 1, the brain function measurement device 1 includes a measurement terminal 2 and a detection unit 3. The measurement terminal 2 includes a control unit 10, a data measurement unit 11, a memory unit 12, an operation unit 13, a display unit 14, and a light source unit 15.

The detection unit 3 and the light source unit 15 are connected by a light irradiation wire 5, while the detection unit 3 and the data measurement unit 11 are connected by a data wire 7.

The control unit 10 is connected to the data measurement unit 11, the memory unit 12, the operation unit 13, the display unit 14, and the light source unit 15, and the memory unit 12 is further connected to the data measurement unit 11 and the display unit 14. In addition, the display unit 14 is also connected to the operation unit 13.

The brain function measurement device 1 with the aforementioned configuration is adapted to, in order to use a property that hemoglobin has different spectral absorption properties in the near-infrared region when carrying oxygen and when not carrying oxygen, have light source probes and a detection probe, which are arranged in the detection unit 3 with predetermined gaps therebetween, fixed on the scalp, and measure temporal changes in the absorbance of a light beam with each wavelength that has propagated through living tissue, thereby estimating the amount of change in oxyhemoglobin in the tissue being observed when oxygen is carried and the amount of change in deoxyhemoglobin in the tissue being observed when oxygen is not carried.

Figure 2:
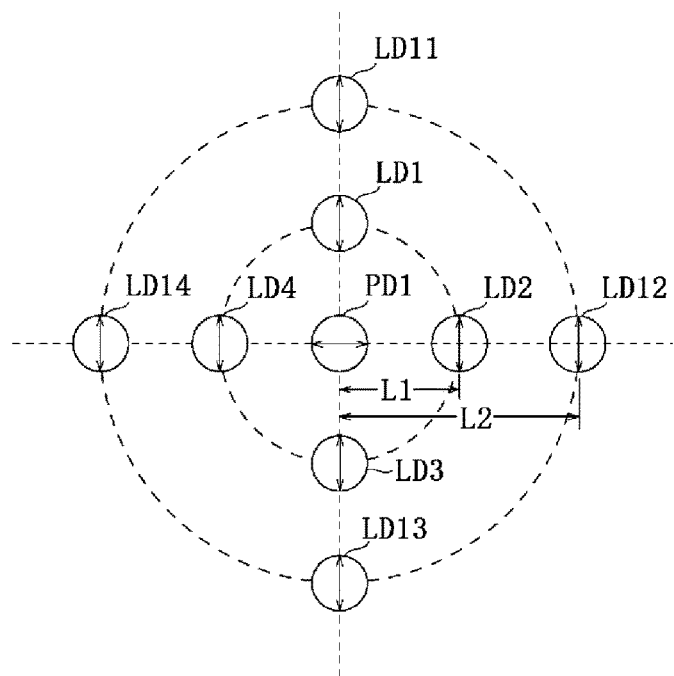
FIG. 2 is a diagram for illustrating an exemplary two-dimensional arrangement pattern of light source probes and a detection probe included in a detection unit 3 illustrated in FIG. 1.

FIG. 2 is a diagram for illustrating an exemplary two-dimensional arrangement pattern of light source probes and a detection probe included in the detection unit 3 illustrated in FIG. 1.

As illustrated in FIG. 2, light source probes LD14, LD4, LD2, and LD12 are sequentially arranged from left in the horizontal direction around a given detection probe PD1 at the center. Among them, the light source probes LD12 and LD14 are each located at a distance of L2 from the detection probe PD1, while the light source probes LD2 and LD4 are each located at a distance of L1 from the detection probe PD1.

In addition, light source probes LD11, LD1, LD3, and LD13 are sequentially arranged from above in the vertical direction around the detection probe PD1 at the center. Among them, the light source probes LD11 and LD13 are each located at a distance of L2 from the detection probe PD1, while the light source probes LD1 and LD3 are each located at a distance of L1 from the detection probe PD1.

It should be noted that the two-dimensional arrangement of the light source probes and the detection probe are adapted to implement the same function even when their mutual positions are exchanged.

Herein, the tip end of each of the light source probes LD1 to LD4 and LD11 to LD14 as well as the detection probe PD1 arranged as above have placed thereon a linearly polarizing film as a polarizing means as described below.

It should be noted that as the linearly polarizing film, a film with an excellent polarization property in the near-infrared region, for example, a wire grid film (WGF) obtained by forming a metal wire grid structure on a sheet is used.

In addition, the polarization directions of the linearly polarizing films are set to the vertical direction for the light source probes LD1 to LD4 and LD11 to LD14 and to the horizontal direction for the detection probe PD1, that is, directions that are orthogonal to one another as indicated by the arrows in FIG. 2.

Figure 3:
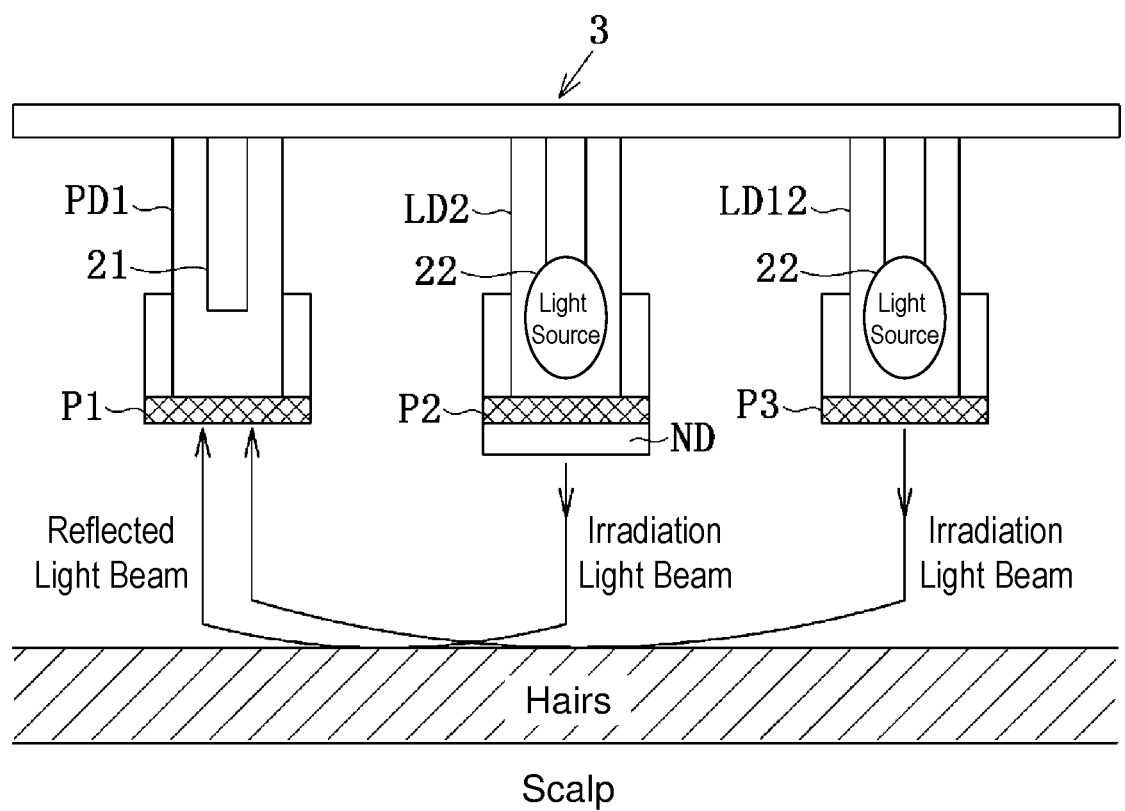
FIG. 3 is a diagram illustrating the cross-sectional structures of a detection probe PD1 and light source probes LD2 and LD12 illustrated in FIG. 2 arranged in the detection unit 3.

FIG. 3 is a diagram illustrating the cross-sectional structures of the detection probe PD1 and the light source probes LD2 and LD12 illustrated in FIG. 2 arranged in the detection unit 3. It should be noted that FIG. 3 illustrates a state in which the detection unit 3 is set on the head, that is, on hairs on the scalp as illustrated in FIG. 1.

As illustrated in FIG. 3, a detector 21 is stored in the detection probe PD1 that is tubular in shape, while a light source 22 is stored in each of the light source probes LD2 and LD12 that are also tubular in shape.

It should be noted that the light source 22 is considered to be a light emitting body of a light beam emitted from the light source unit 15 illustrated in FIG. 1 or a light emitting body itself. Meanwhile, the detector 21 is considered to be a light detecting element itself or a configuration that guides a light beam to the data measurement unit 11 illustrated in FIG. 1 and then measures its intensity.

In addition, as illustrated in FIG. 3, a linearly polarizing film P1 is placed on the tip end of the detection probe PD1 so as to cover a cross section to which the principal axis of the tubular body is normal, and likewise, linearly polarizing films P2 and P3 are placed on the tip ends of the light source probes LD2 and LD12, respectively.

Further, as illustrated in FIG. 3, a neutral-density filter ND is placed in a manner overlapping the linearly polarizing film P2 on the tip end of the light source probe LD2.

Hereinafter, the operation of the brain function measurement device 1 illustrated in FIGS. 1 to 3 will be described with reference to FIG. 4.

In step S1, the scalp of a test subject is irradiated with light beams from the light sources 22 in the light source probes LD2 and LD12. It should be noted that the irradiation is controlled by the control unit 10 in response to an operation input to the operation unit 13 by a user.

In step S2, the light beams emitted in step S1 are linearly polarized in a first direction that is determined by the polarization directions of the linearly polarizing films P2 and P3 placed on the tip ends of the light source probes LD2 and LD12, respectively.

Part of the thus linearly polarized light beams is once reflected by a layer of hairs on the scalp as illustrated in FIG. 3 and then becomes incident on the detector 21 in the detection probe PD1, whereby part of detection signals is generated. Hereinafter, a light beam that becomes incident on the detector 21 in this manner shall be referred to as directly reflected light beam components.

Meanwhile, part of detection signals is also generated from a light beam that becomes incident on the detector 21 after repeating a number of reflections on the hairs. Hereinafter, a light beam that becomes incident on the detector 21 in this manner shall be referred to as multiple-reflected light beam components.

The directly reflected light beam components have properties that the polarized state is preserved and the light intensity is high since no attenuation occurs due to scattering or multiple reflections from living tissue, whereas the light intensity tends to become suddenly low as the distance between the light source 22 and the detector 21 becomes longer.

In contrast, the polarized state of the multiple-reflected light beam components has been converted into that of natural light, and the light intensity is low. Therefore, the difference in the light intensity due to the distance between the light source 22 and the detector 21 is not as large as that of the directly reflected light beam.

One of the reasons that motion artifacts are generated during near-infrared brain function measurement is that the aforementioned two types of reflected light beam components, which have not passed through living tissue, temporally change along with fluctuations of the probes. It is difficult to completely avoid such motion artifacts when measuring a test subject who is not is restrained, in particular.

In recent years, there has been adopted a multidistance probe arrangement method (multidistance measurement) that, in order to further increase the reliability of the near-infrared brain function measurement method, concurrently conducts measurement using one or more of pairs of a light source probe and a detection probe arranged at a short distance therebetween, and extracts signal components derived from a brain tissue layer on the basis of the obtained information.

The aforementioned method is a method of, when the distance between the light source probe and the detection probe is short, referring to a detection signal obtained from the aforementioned pair arranged at a short distance therebetween using a property that a light beam that has not reached the deep tissue of the head is detected, and thus extracting a signal (deep signal) in accordance with the deep tissue of the brain tissue.

However, regarding light beams reflected by hairs, since a signal obtained from a pair of probes arranged at a short distance therebetween is generated in accordance with a light beam that particularly contains a large amount of directly reflected light beam components, there remain the aforementioned fluctuations of the signal resulting from motion artifacts.

Herein, if there exists a technique of reducing the entire light beams reflected by hairs or even reducing only directly reflected light beam components, it becomes possible to not only extract deep signals but also remove motion artifacts in light beams reflected by hairs when using the multidistance probe arrangement method.

Herein, in step S3, with the linearly polarizing film P1, which has a polarization direction (second direction) orthogonal to the polarization direction (first direction) of the linearly polarizing films P2 and P3, placed on the tip end of the detection probe PD1 as illustrated in FIG. 3, the components in the first direction of a reflected light beam, which has been generated as the light beam generated in step S2 is reflected by the head of the test subject, are blocked, using a property that the polarized state of a directly reflected light beam is preserved without becoming that of natural light because the light beam is mirror-reflected on the surface of the hairs.

Then, in step S4, the detector 21 detects the intensity of a light beam generated by the blocking in step S3. It should be noted that the intensity of the light beam detected by the detector 21 is measured by the data measurement unit 11 controlled by the control unit 10, and the obtained data is stored in the storage unit 12 and is displayed on the display unit 14.

By the way, a light beam that that has become incident on brain tissue under the scalp undergoes multiple scattering during the light propagation process since the living tissue is a scatterer with high reflectivity, and thus reaches the detection probe PD1 after being converted into natural light. Then, the light beam with an intensity attenuated to half the original level by the linearly polarizing film P1 illustrated in FIG. 3 is detected by the detector 21.

Therefore, in the detection in step S4, only the directly reflected light beam components that have been generated upon reflection by hairs can be selectively removed.

It should be noted that in the detection in step S4, the detector 21 illustrated in FIG. 3 concurrently detects a reflected light beam of a light beam emitted from the light source probe LD2 (hereinafter referred to as a "first reflected light beam") and a reflected light beam of a light beam emitted from the light source probe LD12 (hereinafter referred to as a "second reflected light beam").

At this time, the intensity of the reflected light beam detected by the detector 21 is higher as the light source probe, which is the irradiation source, is located closer. Herein, the distance between the detector 21 and the light source probe LD12 is L2, the distance between the detector 21 and the light source probe LD2 is L1, and as illustrated in FIGS. 2 and 3, the distance L1 is shorter and the light source probe LD2 is located closer to the detector 21 than is the light source probe LD12. Therefore, the intensity of the first reflected light beam is higher than that that of the second reflected light beam.

Therefore, in order to remove influence, which is derived from the distance from the light source probes LD2 and LD12 to the detector 21, from the detection signal measured with the data measurement unit 11 and normalize the intensities of the first reflected light beam and the second reflected light beam, a neutral-density filter ND is placed in a manner overlapping the linearly polarizing film P2 on the tip end of the light source probe LD2 as illustrated in FIG. 3.

Accordingly, the intensity of the linearly polarized light beam emitted from the light source probe LD2 is reduced, whereby the intensities of the first reflected light beam and the second reflected light beam are normalized, and therefore, a detection signal that is free from influence of the distance from the light source probes LD2 and LD12 to the detector 21 can be obtained.

It should be noted that neutral-density filters ND with the same function are placed on the light source probes whose distances to the detector 21 are equal. Therefore, the neutral-density filter ND placed on the light source probe LD2 whose distance from the detector 21 is L1 is also placed on each of the tip ends of the light source probes LD1, LD3, and LD4 whose distances to the detector 21 are all L1 in FIG. 2, for example.

Figure 4:
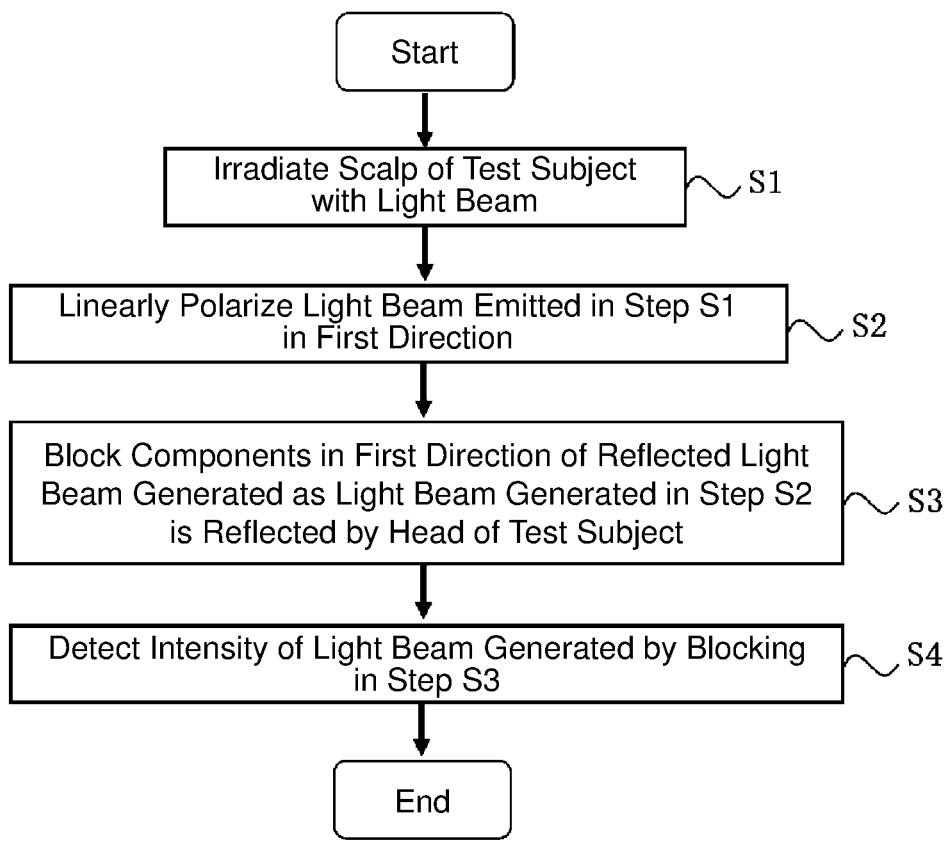
FIG. 4 is a flowchart illustrating a brain function measurement method in accordance with an embodiment of the present invention.

As described above, according to the brain function measurement device 1 in accordance with an embodiment of the present invention and the brain function measurement method in accordance with an embodiment of the present invention illustrated in FIG. 4, it is possible to improve the reliability of measurement of changes in the blood flow derived from brain tissue by removing the aforementioned directly reflected light beam components and thus reducing motion artifacts using a simple configuration or procedure.

REFERENCE SIGNS LIST

1 Brain function measurement device
10 Control unit
11 Data measurement unit
15 Light source unit
21 Detector
22 Light source
LD1 to LD4, LD11 to LD14 Light source probe
PD1 Detection probe
P1 to P3 Linearly polarizing film
ND Neutral-density filter

The invention claimed is:
1. A brain function measurement device, comprising:
a plurality of first light irradiation source probes (LD12) and a plurality of second light irradiation source probes (LD2) for irradiating a scalp of a test subject;
a first linearly polarizing film (P3) mounted on the plurality of first light irradiation source probes (LD12);
a second linearly polarizing film (P2) mounted on the plurality of second light irradiation source probes (LD2);
a dimming filter (ND) mounted on the second linearly polarizing film (P2); and
a detection probe (PD1) including a detector (21) and a third linearly polarizing film (P1) on the detector, wherein the first linearly polarizing film (P3) is configured to linearly polarize first light from the first plurality of light irradiation source probes (LD12) in a first direction, wherein the second linearly polarizing film (P2) is configured to linearly polarize second light from the plurality of second light irradiation source probes (LD2) in the first direction, wherein the third linearly polarizing film (P1) is configured to linearly polarize, in a second direction, the first light from the first plurality of light irradiation source probes (LD12), linearly polarized by the first linearly polarization film (P3), and reflected from the scalp, wherein the third linearly polarizing film (P1) is configured to linearly polarize, in the second direction, the second light from the second plurality of light irradiation source probes (LD2), linearly polarized by the second linearly polarization film (P2), and reflected from the scalp, wherein the second direction is orthogonal to the first direction, wherein the detection probe is configured to detect intensity of the first light from the first plurality of light irradiation source probes (LD12), linearly polarized by the first linearly polarization film (P3), reflected from the scalp and linearly polarized by the third linearly polarization film (P1), wherein the plurality of first light irradiation source probes (LD12) is at a first distance (L12) from the detection probe (PD1) and the plurality of second light irradiation source probes (LD2) is at a second distance (L2) from the detection probe, and wherein the dimming filter (ND) selectively reduces the intensity of the light irradiated from the plurality of second light irradiation source probes (LD2) so as to normalize the intensities of the reflected light detected by the detection probe.

2. The brain function measurement device according to claim 1, wherein the first distance (L12) is longer than the second distance (L2).

3. A brain function measurement method, comprising:

irradiating a scalp of a test subject with a plurality of light beams generated from a plurality of first light irradiation source probes (LD12) and a plurality of second light irradiation source probes (LD2);

linearly polarizing a first light from the plurality of first light irradiation source probes in a first direction by a first linearly polarized film (P2);

linearly polarizing a second light from the plurality of second light irradiation source probes in a first direction by a second linearly polarized film (P3);

selectively lowering an intensity of the second light from the plurality of second light irradiation source probes (LD2) so as to normalize intensities of the first light and the second light by eliminating a distance effect on the intensities between the first light and the second light, wherein the plurality of first light irradiation source probes (LD12) is at a first distance (L12) from a detection probe (PD1) and the plurality of second light irradiation source probes (LD2) is at a second distance (L2) from the detection probe (PD1);

blocking, in a second direction, the first light from the plurality of first light irradiation source probes (LD12), linearly polarized by the first linearly polarization film (P3), and reflected from the scalp, and the second light from the second plurality of light irradiation source probes (LD2), linearly polarized by the second linearly polarization film (P2), and reflected from the scalp, wherein blocking the light waves comprises providing a third polarizing film (P1) on the detector probe, wherein the third linearly polarizing film (P1) is configured to linearly polarize the first light and the second light, wherein the first direction and the second direction are orthogonal; and detecting intensities of light beams generated by the blocking in the detection probe.

4. The brain function measurement method according to claim 3, wherein the first distance (L12) is longer than the second distance (L2).

* * * * *